United States Patent [19]
O'Laughlin et al.

[11] Patent Number: 5,642,744
[45] Date of Patent: Jul. 1, 1997

[54] UROSTOMY COLLECTOR CLEANING ATTACHMENT

[76] Inventors: Gavin S. O'Laughlin, 4939 Lake Shore Dr., Richton Park, Ill. 60471; Patrick K. O'Laughlin, 22600 Sherman Rd., Chicago Heights, Ill. 60411

[21] Appl. No.: 642,785

[22] Filed: May 3, 1996

[51] Int. Cl.⁶ ............................ B08B 3/02; B08B 9/08
[52] U.S. Cl. ........................ 134/166 R; 604/332
[58] Field of Search ............... 134/166 R, 166 C, 134/169 R, 169 C; 604/277, 332, 334; 141/382, 383, 385; 285/319, 320, 921

[56] References Cited

U.S. PATENT DOCUMENTS

| | | |
|---|---|---|
| 1,348,277 | 8/1920 | Gerrish. |
| 1,383,008 | 6/1921 | Myers. |
| 2,223,566 | 12/1940 | Koch ............................. 604/334 X |
| 2,782,785 | 2/1957 | Arcand ........................... 604/334 |
| 3,526,416 | 9/1970 | Kish ............................... 285/2 |
| 4,194,506 | 3/1980 | Voorhies ......................... 128/283 |
| 4,462,510 | 7/1984 | Steer .............................. 222/48 |
| 4,607,868 | 8/1986 | Harvey ........................... 285/332 |
| 4,787,429 | 11/1988 | Valentini et al. ................ 141/383 |
| 5,083,580 | 1/1992 | Lash .............................. 134/113 |
| 5,096,503 | 3/1992 | Wellman ........................ 134/22.18 |
| 5,165,727 | 11/1992 | Valley ............................ 285/12 |
| 5,398,365 | 3/1995 | MacKenzie .................... 15/160 |
| 5,470,325 | 11/1995 | Fundock ........................ 604/332 |

FOREIGN PATENT DOCUMENTS

| | | | |
|---|---|---|---|
| 2046097 | of 1908 | United Kingdom ............. 604/277 |
| 2258399 | 2/1993 | United Kingdom ............. 604/334 |

*Primary Examiner*—Philip R. Coe
*Attorney, Agent, or Firm*—Don Moyer

[57] ABSTRACT

The cleaning attachment mates with a standard urostomy collector connector, has a hose barb which is secured by the urostomy connector jaws, and mates with a standard household faucet so that water can flow through the cleaning attachment through the urostomy connector, and onto the urostomy collector bag for cleaning the collector.

3 Claims, 1 Drawing Sheet

UROSTOMY COLLECTOR CLEANING ATTACHMENT

BACKGROUND OF THE INVENTION

This invention is a cleaning attachment which removably couples a standard urostomy collector connector to a standard household faucet in order to clean the urostomy collector.

A standard urostomy collector shown by Steer in U.S. Pat. No. 4,462,510 is now in common use. Fluid enters through the standard connector and passes into the collector bag through tubing which is sealed into the bag. Because this standard urostomy collector connector does not mate with any readily available household water source, there is no easy way to flush the collector tube and collector bag with water in order to clean the tube and bag.

Implements to aid cleaning of ostomy devices are shown by Voorhies in U.S. Pat. No. 4,194,506, by Lash in U.S. Pat. No. 5,083,580, and by Wellnam in U.S. Pat. No. 5,096,503. None of these suggest an attachment which mates with the standard urostomy collector connector and which mates with a household water faucet.

Various kinds of fluid flow couplers have been shown. For example, by Gerish in U.S. Pat. No. 1,348,277; by Myers in U.S. Pat. No. 1,383,008; by Kish in U.S. Pat. No. 3,526,416; by Harvey in U.S. Pat. No. 4,607,868; by Valley in U.S. Pat. No. 5,165,727; and by MacKenzie in U.S. Pat. No. 5,398,365. None of these suggest an attachment which easily mates with the standard urostomy collector connector and which mates with a household water faucet.

Thus, there is a clear need for a cleaning attachment which will couple a household water source to the standard urostomy collector connector in order to use the household water source for cleaning the collector.

SUMMARY OF THE INVENTION

Objects of this invention include the following. Make a urostomy collector cleaning attachment which can be attached securely and removably to a standard urostomy collector connector. Make a urostomy collector cleaning attachment which can be attached securely and removably to a household faucet. Make a urostomy collector cleaning attachment which is easy to use, easy to manufacture, and low in cost.

In summary, one embodiment of this invention is a hollow nozzle which can be removably fitted into a standard urostomy collector connector, the nozzle having a hose barb on the nozzle, the barb being removably securable by jaws on the urostomy connector, and the nozzle having a faucet connector attached to the nozzle for removably connecting the nozzle to a standard household water faucet so that water can flow through the nozzle to the collector.

Other equivalent embodiments will be comprehended in the detailed description of the drawings, which will make additional equivalent embodiments obvious to people skilled in the art.

DRAWING FIGURES

DETAILED DESCRIPTION OF THE DRAWINGS

Figure 1:
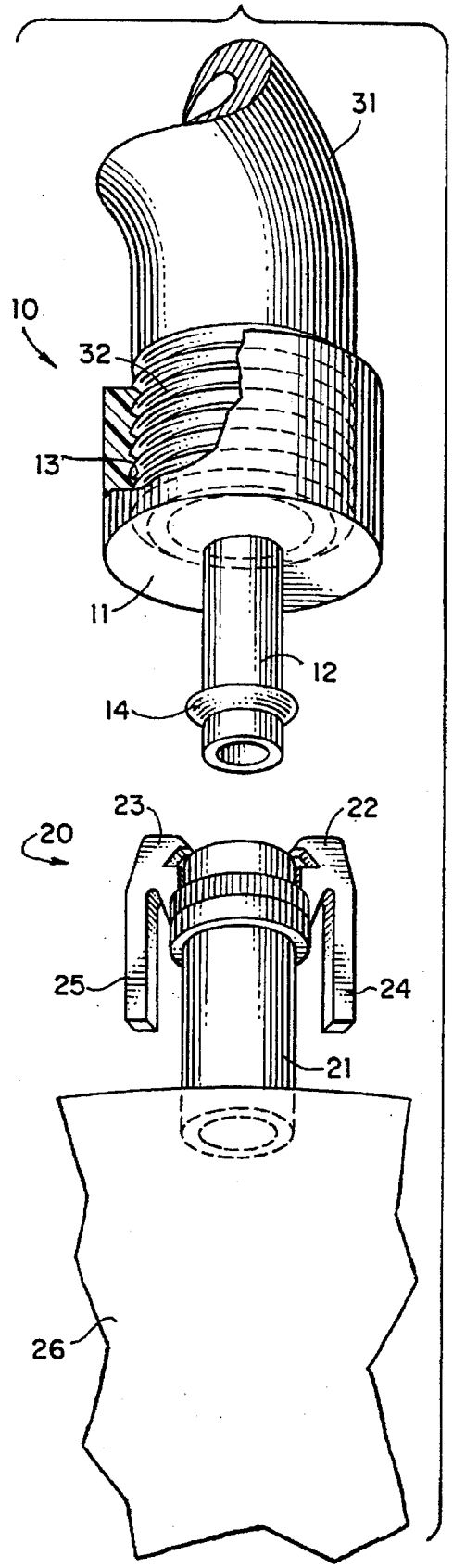
FIG. 1 shows the new attachment threaded onto external standard hose threads on a household faucet and shows the standard urostomy collector connector.
Figure 2:
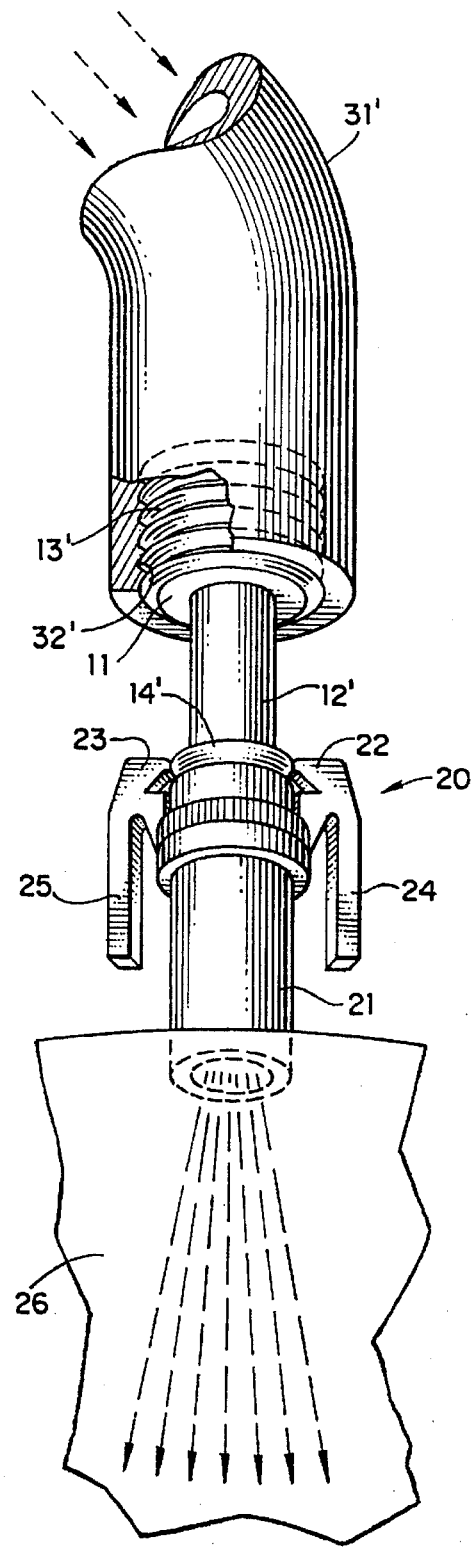
FIG. 2 shows another embodiment of the new attachment threaded into internal standard aerator threads on a standard household water faucet and shows the attachment connected to the standard urostomy collector connector.

The new urostomy collector cleaning attachment 10 has a faucet connector 11 which has internal standard hose threads 13 which can be threaded onto matching external standard hose threads 32 on a standard household faucet 31. Another embodiment shown in FIG. 2 has a faucet connector 11' which has external standard aerator threads 13' which can be threaded into matching internal standard aerator threads 32' on a standard household faucet 31'. Other equivalent means for connecting the new attachment to household faucets will be obvious to people skilled in the art.

A standard urostomy collector 20 shown in U.S. Pat. No. 4,462,510 is now in common use. Fluid can flow into the collector bag 26 via a standard urostomy collector connector 21. Both embodiments of the new cleaning attachment have a hollow nozzle 12 and 12' which can fit into the standard urostomy collector connector 21. The nozzle has a hose barb 14 and 14' which encircles the nozzle, extends radially away from the nozzle, is not inclined toward the faucet connector 11 and 11', and is inclined toward the end of the nozzle which is insertable into the urostomy collector connector 21. When the nozzle is connected to the standard urostomy collector connector 21 a first securing jaw 22 on the connector 21 and a second securing jaw 23 on the connector 21 engage the hose barb 14 or 14' and secure the nozzle in the connector 21. To remove the connector 21 from the nozzle 12 or 12' a first arm 24 on the first jaw 22 and a second arm 25 on the second jaw 23 are pushed to open the jaws 22 and 23 and disengage the jaws from the hose barb 14 or 14'.

In the preferred embodiment the faucet connector 11 has a 1.292 inches outside diameter and is 0.755 inches in length. The nozzle 12 and 12' has an outside diameter of 0.340 inches, has an inside diameter of 0.235 inches, and is 0.370 inches in length from the end which is inserted into the urostomy collector connector to the hose barb. The hose barb 14 and 14' is 0.075 inches in length along the nozzle and extends outward from the nozzle to a diameter of 0.440 inches.

Other equivalent forms for the cleaning attachment and other equivalent means for attaching the cleaning attachment to a water source will be obvious to people skilled in the art. It is understood therefore that this invention is not limited to the particular examples illustrated here.

We claim:

1. In combination with a standard urostomy collector having a standard urostomy collector connector, the standard urostomy collector connector having a first securing jaw and having a second securing jaw, a new urostomy collector cleaning attachment comprising:

a hollow nozzle which can be removably fitted into the standard urostomy collector connector;

a hose barb on the nozzle which can be removably secured by the first securing jaw of the standard urostomy collector connector and by the second securing jaw of the standard urostomy collector connector; and a faucet connector attached to the nozzle, the faucet connector for removably connecting the nozzle to a standard household water faucet so that water from the faucet can flow through the nozzle, through the standard urostomy collector connector to the standard urostomy collector.

2. The urostomy collector cleaning attachment of claim 1 wherein the faucet connector has internal standard hose threads for removably connecting the nozzle to a household water faucet having external standard hose threads.

3. The urostomy collector cleaning attachment of claim 1 wherein the faucet connector has external standard aerator threads for removably connecting the nozzle to a household faucet having internal standard aerator threads.

* * * * *